(12) United States Patent
Farmer et al.

(10) Patent No.: US 11,155,746 B2
(45) Date of Patent: Oct. 26, 2021

(54) COMPOSITIONS AND METHODS FOR REDUCING HYDROGEN SULFIDE AND MICROBIAL INFLUENCED CORROSION IN CRUDE OIL, NATURAL GAS, AND IN ASSOCIATED EQUIPMENT

(71) Applicant: LOCUS OIL IP COMPANY, LLC, Solon, OH (US)

(72) Inventors: Sean Farmer, North Miami Beach, FL (US); Ken Alibek, Solon, OH (US); Karthik N. Karathur, Solon, OH (US); Anthony Nerris, Solon, OH (US); Martin R. Shumway, Solon, OH (US); Nicholas Callow, Solon, OH (US); Ryan McGonagle, Solon, OH (US); Don Kreager, Solon, OH (US); Yajie Chen, Solon, OH (US)

(73) Assignee: LOCUS OIL IP COMPANY, LLC, Solon, OH (US)

( * ) Notice: Subject to any disclaimer, the term of this patent is extended or adjusted under 35 U.S.C. 154(b) by 0 days.

(21) Appl. No.: 16/477,892

(22) PCT Filed: Feb. 8, 2018

(86) PCT No.: PCT/US2018/017408
§ 371 (c)(1),
(2) Date: Jul. 14, 2019

(87) PCT Pub. No.: WO2018/148397
PCT Pub. Date: Aug. 16, 2018

(65) Prior Publication Data
US 2020/0123433 A1    Apr. 23, 2020

Related U.S. Application Data

(60) Provisional application No. 62/456,979, filed on Feb. 9, 2017, provisional application No. 62/463,864, filed
(Continued)

(51) Int. Cl.
*C09K 8/54* (2006.01)
*C09K 8/532* (2006.01)
(Continued)

(52) U.S. Cl.
CPC ............... *C09K 8/54* (2013.01); *C09K 8/532* (2013.01); *C09K 8/582* (2013.01); *C09K 8/584* (2013.01);
(Continued)

(58) Field of Classification Search
None
See application file for complete search history.

(56) References Cited

U.S. PATENT DOCUMENTS

| 4,450,908 A | 5/1984 | Hitzman |
| 4,522,261 A | 6/1985 | McInerney et al. |

(Continued)

FOREIGN PATENT DOCUMENTS

| CN | 101839126 A | 9/2010 |
| CN | 102352227 A | 2/2012 |

(Continued)

OTHER PUBLICATIONS

Amosa, M.K., et al., "Sulphide Scavengers in Oil and Gas Industry—A Review." NAFTA, 2010, 61(2): 85-92.
(Continued)

*Primary Examiner* — Jeffrey D Washville
(74) *Attorney, Agent, or Firm* — Saliwanchik, Lloyd & Eisenschenk

(57) ABSTRACT

The present invention provides compositions and methods for reducing hydrogen sulfide and/or mercaptans in oil
(Continued)

and/or natural gas as well as for reducing microbial induced corrosion ("MIC") in oil and gas production environments. In particular, the subject invention provides environmentally-friendly compositions and methods for reducing hydrogen sulfide in oil and natural gas environments by controlling biocorrosive bacteria, such as SRB, therein.

10 Claims, 1 Drawing Sheet

Related U.S. Application Data on Feb. 27, 2017, provisional application No. 62/507,904, filed on May 18, 2017, provisional application No. 62/528,731, filed on Jul. 5, 2017.

(51) Int. Cl.
| | |
|---|---|
| C09K 8/582 | (2006.01) |
| C09K 8/584 | (2006.01) |
| C10G 75/04 | (2006.01) |
| C12N 1/20 | (2006.01) |

(52) U.S. Cl.
CPC .......... *C10G 75/04* (2013.01); *C09K 2208/20* (2013.01); *C09K 2208/32* (2013.01); *C12N 1/20* (2013.01)

(56) References Cited

U.S. PATENT DOCUMENTS

| | | | |
|---|---|---|---|
| 4,905,761 A | 3/1990 | Bryant | |
| 5,165,477 A | 11/1992 | Shell et al. | |
| 6,033,901 A | 3/2000 | Powell, Jr. | |
| 9,422,470 B2 | 8/2016 | Xu et al. | |
| 9,441,115 B2 | 9/2016 | Wu et al. | |
| 9,683,164 B2 | 6/2017 | Gunawan et al. | |
| 10,023,787 B2 | 7/2018 | Benoit et al. | |
| 2009/0029879 A1 | 1/2009 | Soni et al. | |
| 2010/0044031 A1 | 2/2010 | Fallon et al. | |
| 2012/0122740 A1 | 5/2012 | Roldan Carrillo et al. | |
| 2012/0214713 A1 | 8/2012 | Mu et al. | |
| 2013/0062053 A1 | 3/2013 | Kohr et al. | |
| 2013/0324406 A1 | 12/2013 | Chisholm et al. | |
| 2014/0360727 A1 | 12/2014 | Milam et al. | |
| 2015/0037302 A1 | 2/2015 | Bralkowski et al. | |
| 2015/0045290 A1 | 2/2015 | Coutte et al. | |
| 2016/0251565 A1 | 9/2016 | Yanagisawa et al. | |
| 2017/0283685 A1* | 10/2017 | Coates | C09K 8/54 |

FOREIGN PATENT DOCUMENTS

| | | |
|---|---|---|
| CN | 102766579 A | 11/2012 |
| CN | 104109646 A | 10/2014 |
| CN | 105753283 A | 7/2016 |
| WO | 2016097857 A1 | 6/2016 |
| WO | 2017044953 A1 | 3/2017 |

OTHER PUBLICATIONS

Castaneda, L.C., et al., "Current situation of emerging technologies for upgrading of heavy oils." Catalysis Today, 2014, 220-222: 248-273.

De Almeida, D., et al., "Biosurfactants: Promising Molecules for Petroleum Biotechnology Advances." Frontiers in Microbiology, Oct. 2016, 7(1718): 1-14.

De Brito, D., Biosurfactants from renewable raw materials, Universidade do Minho Departamento de Engenharia Biologica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

Elshafie, A. E., et al., "Sophorolipids Production by Candida bombicola ATCC 22214 and its Potential Application in Microbial Enhanced Oil Recovery." Frontiers in Microbiology, Nov. 2015, 6(1324): 1-11.

El-Sheshtawy, H.S., et al., "Production of biosurfactants by Bacillus licheniformis and Candida albicans for application in microbial enhanced oil recovery." Egyptian Journal of Petroleum, 2016, 25: 293-298.

Ghojavand, H. et al., "Isolation of thermotolerant, halotolerant, facultative biosurfactant-producing bacteria." Appl. Microbiol. Biotechnol, Oct. 2008, 80(6): Abstract, doi: 10,1007/s00253-008-1570-7.

Gudina, E., et al., "Biosurfactant-producing and oil-degrading Bacillus subtilis strains enhance oil recovery in laboratory sand-pack columns." Journal of Hazardous Materials, 2013, 261: 106-113.

Morikawa, M., "Beneficial Biofilm Formation by Industrial Bacteria *Bacillus subtilis* and Related Species." Journal of Bioscience and Bioengineering, 2006, 101(1): 1-8.

Nitschke, M., et al., "Production and properties of a surfactant obtained from Bacillus subtilis grown on cassava wastewater." Bioresource Technology, 2006, 97: 336-341.

Nur, H.A., et al., "*Saccharomyces cerevisiae* from Baker's Yeast for Lower Oil Viscosity and Beneficial Metabolite to Improve Oil Recovery: An Overview." Applied Mechanics and Materials, 2014, 625: 522-525.

Rocha E Silva, F.C.P., et al., "Yeasts and bacterial biosurfactants as demulsifiers for petroleum derivative in seawater emulsions." AMB Expr., 2007, 7(202): 1-13.

Sen, R., "Biosurfactants: Advances in Experimental Medicine and Biology." Landes Bioscience and Springer Science+Business Media, LLC, 2010, 672: 1-331.

Sharma, A. et al., "A study on biosurfactant production in *Lactobacillus* and *Bacillus* sp." Int. J. Curr. Microbiol. App. Sci., 2014, 3(11): 723-733.

Silva, R., et al., "Applications of Biosurfactants in the Petroleum Industry and the Remediation of Oil Spills." International Journal of Molecular Sciences, 2014, 15: 12523-12542.

Thaniyavarn, J., et al., "Production of Sophorolipid Biosurfactant by Pichia anomala." Bioscience, Biotechnology, and Biochemistry, 2008, 72(8): 2061-2068.

Youssef, N., et al., "In Situ Biosurfactant Production by Bacillus Strains Injected into a Limestone Petroleum Reservoir." Applied and Environmental Microbiology, 2007, 73(4): 1239-1247.

\* cited by examiner

COMPOSITIONS AND METHODS FOR REDUCING HYDROGEN SULFIDE AND MICROBIAL INFLUENCED CORROSION IN CRUDE OIL, NATURAL GAS, AND IN ASSOCIATED EQUIPMENT

CROSS-REFERENCE TO RELATED APPLICATIONS

This application is a National Stage Application of International Application No. PCT/US2018/017408, filed Feb. 8, 2018: which claims the benefit of the following U.S. provisional applications: Ser. No. 62/456,979, filed Feb. 9, 2017; Ser. No. 62/463,864, filed Feb. 27, 2017; Ser. No. 62/507,904, filed May 18, 2017; and Ser. No. 62/528,731, filed Jul. 5, 2017, each of which is incorporated herein by reference in its entirety.

BACKGROUND OF THE INVENTION

Hydrocarbon compositions are critical resources for the production of fuels, lubricants, plastics, and countless other products. Because of the high demand for hydrocarbon compositions, the safety and efficiency of their production and transmission is essential. One major factor affecting the safety and efficiency of crude oil and natural gas production is the presence of hydrogen sulfide ($H_2S$) gas. $H_2S$ gas is found naturally in petroleum and natural gas in low amounts; however, when $H_2S$ levels become high the oil or gas is said to become "sour."

Hydrogen sulfide is a concern in the oil and gas industry for a variety of reasons. For example, $H_2S$ can become an air pollutant near petroleum refineries and in oil and gas extraction areas. Atmospheric releases of $H_2S$ represent a significant public health concern. $H_2S$ is extremely toxic. Exposure to concentrations above 100 ppm can cause damage to internal organs, and exposures above 600 ppm can be rapidly fatal.

Another group of sulfur-containing compounds can be present in oil and gas fields as well. Known as mercaptans, these organosulfur compounds contain a carbon-bonded sulfhydryl group and are found in many hydrocarbon streams, mainly as an impurity. They are similar to alcohols, but with a sulfur (S) atom replacing the oxygen atom. Some mercaptans present strong odors and can cause serious disruptions to daily life. Humans are highly sensitive to mercaptans at very low levels. For this reason, mercaptans are used as odorizers in consumer and commercial natural gas to signal gas leaks. Some mercaptans can cause corrosion, and often lead to copper strip test failures under certain conditions. Mercaptans can also negatively affect catalysis and solid adsorption beds, such as silica gel or alumina, by competing for access to the same active sites. Mercaptan removal is necessary for reducing sulfur emissions, as combustion and emission of mercaptan-containing compounds will lead to SOx formation.

Aside from direct health concerns, $H_2S$ and mercaptans cause corrosion of oil and gas production and transmission equipment. Corrosion of pipes, valves, fittings and tanks can cause a breakdown of oil and gas gathering systems and can be a serious threat to employees and to the public. Also, repairing and replacing corroded equipment can lead to substantial expense.

Corrosion that results from the presence of microorganisms, i.e., microbial induced corrosion (MIC), is a significant problem for oil and gas production and transmission. When surfaces in a well, or other surfaces are exposed to natural environments, they are rapidly colonized by bacteria that are naturally present in the surrounding environment, which in turn can form a biofilm. The upper layers of biofilm are mostly aerobic while the regions underneath could be anaerobic due to the depletion of oxygen by the biofilm.

Certain microorganisms can colonize these anaerobic niches and produce byproducts that reduce the quality of crude oil and natural gas, cause corrosion of metals, and pose a significant threat to health and the environment. MIC has been implicated in the deterioration of metals in, for example, pipelines and off-shore oil rigs in the oil and shipping industries. Other environments are affected as well, including cooling water recirculation systems in industrial settings and sewage treatment facilities and pipelines.

Microorganisms that are responsible for MIC include sulfate-reducing bacteria ("SRB") and acid producing bacteria ("APB"). APB produce corrosion-inducing compounds through anaerobic fermentation. These compounds can include organic acids, such as volatile fatty acids, and alcohols. As a result of organic acid production, the pH underneath an APB biofilm can be considerably lower than that of the bulk fluid, thus contributing to deterioration of the structures on which the bacteria grow.

SRB and archaea obtain energy by oxidizing organic compounds or molecular hydrogen ($H_2$) while reducing sulfate ($SO^{2-4}$) to $H_2S$. In a sense, these organisms "breathe" sulfate rather than oxygen in a form of anaerobic respiration. Most SRB can also reduce other oxidized inorganic sulfur compounds, such as sulfite, thiosulfate, or elemental sulfur to hydrogen sulfide.

SRB contribute significantly to increased $H_2S$ and mercaptan concentrations in crude oil and natural gas, thereby impacting the quality of the oil and gas, as well as the safety and integrity of oilfield and natural gas equipment and production. Additionally, SRB production of $H_2S$ leads to progressive corrosion of iron in anoxic, sulfate-rich environments. SRB can also corrode iron by direct utilization of the metal itself, which is likely the primary process driving iron corrosion in sulfate-containing anoxic environments.

Furthermore, $H_2S$ produced by SRB is metabolized by sulfur-oxidizing organisms, such as *Thiobacillus*, into sulfuric acid—one of the strongest acids known. Sulfuric acid degradation can cause extreme damage to pipes and other equipment used in the oil and gas industries, and has been found to cause billions of dollars in corrosion damage each year in the U.S.

The preferred biocorrosion-eliminating strategy depends on which organisms are present in the environment being treated. For example, susceptibility of archaea to antimicrobial agents is different from susceptibility of proteobacteria. Archaea are characterized by, for example, their broad-spectrum resistance to antimicrobial agents. Specifically, the walls of archaea lack peptidoglycan (thus, they are Gram-negative), making them resistant to many antimicrobial agents that interfere with peptidoglycan biosynthesis. Archaea are susceptible, however, to antimicrobial agents that interfere with protein synthesis.

On the other hand, proteobacteria can have differing susceptibilities and/or resistance due to other factors such as, for example, the types of peptidoglycan they contain, the presence of capsules, spore-formation, and modification of molecular targets. Thus, in light of these differences, the development and application of a broad-spectrum antibacterial strategy with high efficacy is desirable to eliminate corrosive bacteria and reduce $H_2S$ in crude oil, natural gas and wellbore brine.

Conventional corrosion inhibition strategies involve a variety of strategies. These include modification in the pH, redox potential, and/or resistivity of the environment in which the equipment is to be installed; inorganic coatings; cathodic protection; and the use of "traditional" biocides. However, many of these strategies are not practical in oil and gas production operations.

Of these methods for combatting biocorrosion, the most common methods generally include traditional biocides. Oxidizing biocides, such as chlorinating compounds, can be used in some systems, as well as non-oxidizing biocides, such as amine-type compounds and aldehydes. Non-oxidizing biocides are more stable and can be used in a variety of environments. Despite the fact that biocides are commonly used, the costs of the biocides, and the potential harm caused by releasing large quantities of inorganic compounds into the environment, are significant.

An alternative method, which has become popular in recent years, is nitrate treatment. Nitrate technology is based on selective growth of nitrate-reducing bacteria ("NRB"), which replace the harmful SRB and reduce the ability of SRB to grow extensively. Many of the nitrate compounds are soluble in water, do not dissolve in oil, are not sensitive to salt levels, and have low toxicity. Also, nitrate compounds can be completely consumed, their activity increases with time, and they are not temperature-sensitive.

Even though the unit cost of nitrates is not high, the cost of treatment on a large scale, such as in an oil and gas setting, can be extremely high. Furthermore, nitrate treatments have other drawbacks. For example, they can be inefficient for gravity lines and can increase nitrogen levels in wastewater. Additionally, resultant $N_2$ gas (or residual $NO_3$) may present problems for water treatment plants; costs for the prevention mode may be excessive in long retention time lines, which may be impacted by high BOD levels; and the bio-mediated oxidation mode may require several hours, making nitrates less effective in certain applications.

Thus, damage to the petroleum and natural gas industries caused by MIC, in particular damage caused by $H_2S$, remains profound. Each year these industries experience many billions of dollars' worth of loss due to the effects of corrosion, the need for cleaning "sour" natural gas and crude oil, and the implementation of measures to reduce various environmental hazards caused by $H_2S$.

As noted above, many biocide treatments are not environmentally friendly and are not highly efficient. Nitrate treatments can be safer and more effective, but they can come with significant costs.

Thus, there is a need in the art for an effective, environmentally-friendly, and economically-acceptable means for reducing $H_2S$ and mercaptans, and preventing or inhibiting SRB growth in oil and gas formations and on the surfaces of the equipment used in all aspects of oil and gas production.

BRIEF SUMMARY OF THE INVENTION

The subject invention provides environmentally-friendly compositions and methods to reduce and/or eliminate hydrogen sulfide ($H_2S$) and other sulfur-containing compounds in oil and natural gas while simultaneously enhancing oil recovery. In one embodiment, this is achieved by the efficient control of sulfate reducing bacteria (SRB). The compositions and methods can also be used for reducing the "sourness" of crude oil and gas.

The present invention further provides compositions and methods for reducing and/or eliminating microbial induced corrosion ("MIC").

The methods and compositions can be used in the oil and gas industry, agriculture, environmental cleanup, and other industries where biofilm and other microbial growth causes complications such as, for example, production of toxic byproducts such as $H_2S$ and mercaptans, corrosion of equipment, and reduction in quality of manufactured products.

In certain embodiments, the subject invention provides materials and methods for improving the quality of oil and/or gas while enhancing oil recovery, by treating drilling sites with compositions comprising microorganisms and/or their by-products.

In preferred embodiments, a first composition is provided for reducing $H_2S$ and controlling biocorrosive bacteria present in oil and natural gas production environments while enhancing oil recovery, wherein the first composition comprises an antimicrobial biosurfactant blend, a chelating agent, and one or more $H_2S$ scavengers.

In some embodiments, the antimicrobial biosurfactant blend comprises one or more biosurfactants. The one or more biosurfactants can include glycolipids such as, for example, sophorolipids, rhamnolipids, and/or a combination thereof. Advantageously, the biosurfactants can be used at relatively low concentrations to inhibit the growth of bacteria, particularly, Gram-positive bacteria.

In some embodiments, the antimicrobial biosurfactant blend further comprises one or more lipopeptide biosurfactants, such as, for example, surfactin. The use of surfactin broadens the spectrum of antimicrobial activity to include Gram-negative bacteria.

In some embodiments, the first composition further comprises a chelating agent. In specific embodiments, the chelating agent is EDTA.

In some embodiments, the first composition further comprises one or more $H_2S$ scavengers capable of converting $H_2S$ into more inert forms. The one or more $H_2S$ scavengers can be, for example, nitrate or nitrite solutions. In specific embodiments, the $H_2S$ scavengers are selected from nitrate or nitrite salts, including but not limited to, sodium nitrate, sodium nitrite, ammonium nitrate, ammonium nitrite, potassium nitrate, and potassium nitrite. In another embodiment, the $H_2S$ scavenger can include glyoxal.

In certain embodiments, the first composition can comprise one or more natural biological substances with known antimicrobial properties, particularly against Gram-negative microorganisms. In one embodiment, the natural biological substance can comprise nisin, an antimicrobial polypeptide obtained by cultivation of *Lactococcus lactis*. In another embodiment, the natural biological substance can comprise citronella (lemongrass extract). Citronella can be used for suppressing both Gram-negative and Gram-positive bacteria, as well as some fungi and yeasts.

In one embodiment, a second composition is provided for stabilizing and prolonging the antimicrobial and hydrogen sulfide-reducing effects, as well as the enhanced oil recovery, of the first composition, for example, by preventing any remaining SRB from multiplying.

The second composition can comprise a microorganism capable of outcompeting residual SRB for common carbon and energy sources, thereby suppressing the regrowth of SRB; and, optionally, nutrient sources for ensuring effective growth of the microbial culture in anaerobic conditions, including but not limited to, nitrites, nitrates, phosphorus, magnesium, protein sources and/or carbon.

Preferably, the microorganism of the second composition is in spore form. Accordingly, in one embodiment, the second composition can comprise substances for enhancing germination of spores, such as, for example, L-alanine and/or manganese.

In one embodiment, the microorganism of the second composition is a spore-forming, biosurfactant-producing strain of bacteria. In preferred embodiments, the bacteria can be introduced as nitrate-reducing bacteria ("NRB").

In one embodiment, the bacteria is a species of the *Bacillus* clade. In one embodiment, the bacteria is a species of the *Pseudomonas* clade. In preferred embodiments, the bacteria of the second composition is a strain of *Bacillus subtilis*. Even more specifically, the *Bacillus subtilis* can be *B. subtilis* var. locuses strains B1 and/or B2, which are effective producers of the lipopeptide surfactin.

In one embodiment, the bacteria is a strain of *Pseudomonas*, such as, for example, *P. aeruginosa*. *P. aeruginosa* is an effective producer of rhamnolipid biosurfactants.

In one embodiment, the first and second compositions can be used to inhibit $H_2S$ production by SRB and other biocorrosive bacteria while enhancing oil and/or gas recovery. Advantageously, the compositions can have broad-spectrum antimicrobial properties, meaning they can be used to control, for example, both Gram-positive and Gram-negative bacteria, as well as other biocorrosive microorganisms. In one embodiment, the biocorrosive bacteria are in the form of a biofilm.

In one embodiment, the first and second compositions can be used to reduce the corrosion and deterioration of metal equipment and structures in, and on, which biocorrosive bacteria grow, specifically, corrosion and deterioration of equipment and structures used for crude oil and natural gas production.

In one embodiment, a two-phase method is provided for improving oil and natural gas production. Specifically, the methods can be used to inhibit $H_2S$ production by SRB and other biocorrosive bacteria, as well as reduce the "sourness" of crude oil and gas, while simultaneously enhancing oil and gas recovery. The methods can further be used to reduce the conversion of sweet oil to sour oil and gas, increase the conversion of sour oil and gas to sweet oil and gas, and/or preserve the sweetness of oil and gas. The methods can further be used to reduce the content of $H_2S$ and mercaptans in oil within or outside of a well.

In certain embodiments, the two-phase method can further be used for reducing and/or eliminating microbial induced corrosion ("MIC") of equipment and structures used for crude oil and natural gas production.

In one embodiment, phase one of the method comprises applying the first composition of the subject invention to an oil and gas containing formation, for example, by injecting the first composition as deeply as possible into a wellbore; shutting in the formation; pumping out the composition; and opening the formation to resume oil and/or gas recovery.

Preferably, phase one is carried out while continuously monitoring hydrogen sulfide levels within the formation.

In one embodiment of phase one, the step of shutting in the formation is carried out until the level of hydrogen sulfide reduces to a desired concentration. For example, the shut in period can endure for about 3 to about 60 days, or until the hydrogen sulfide levels reduce to a concentration of about 0 ppm to about 50 ppm, preferably from about 0 ppm to about 25 ppm.

Phase one of the method can serve as an initial treatment to (a) control biocorrosive bacteria, (b) reduce $H_2S$ concentration in the formation, and (c) enhance oil and gas recovery from the formation.

In one embodiment, phase two of the method comprises recovering oil and/or gas from the formation until an increase of hydrogen sulfide concentration is observed; applying the second composition of the subject invention to the formation, for example, by injecting it as deeply as possible into the wellbore; shutting in the formation; and opening the formation to resume oil and/or gas recovery.

Preferably, phase two is carried out while continuously monitoring hydrogen sulfide levels within the formation.

In one embodiment, the increase of hydrogen sulfide concentration that is observed prior to application of the second composition in phase two is an increase of from about 1 ppm to about 50 ppm to about 100 ppm, or higher, above the lowest observed concentration. In one embodiment, the increase of hydrogen sulfide concentration that is observed prior to application of the second composition is any increase that brings the concentration of hydrogen sulfide to a level of about 50 to about 100 ppm, or higher.

In one embodiment of phase two, the step of shutting in the formation is carried out until the level of hydrogen sulfide reduces to a desired concentration. For example, the shut in period can endure for about 3 to about 60 days, or until the hydrogen sulfide levels reduce to a concentration of about 0 ppm to about 50 ppm, preferably from about 0 ppm to about 25 ppm.

Phase two of the method can serve to enhance the control of biocorrosive bacteria, reduction in hydrogen sulfide concentration, and enhanced oil and gas recovery. Phase two can also serve to stabilize and prolong the antimicrobial and hydrogen sulfide-reducing effects of phase one, for example, by preventing any remaining SRB from multiplying.

In one embodiment of the subject method, only phase one is employed without phase two. In one embodiment, phase two is employed without phase one beforehand.

Advantageously, the present invention can be used without releasing large quantities of inorganic compounds into the environment. Additionally, the compositions and methods utilize components that are biodegradable and toxicologically safe. Thus, the present invention can be used in oil and gas production (and other industries) as a "green" treatment.

DETAILED DESCRIPTION OF THE INVENTION

Figure 1:
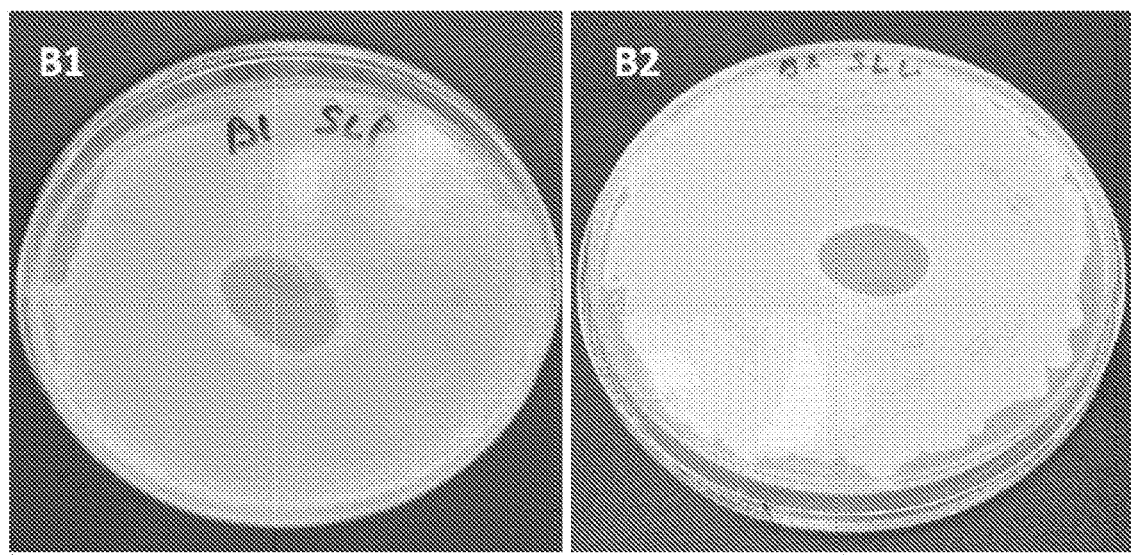
FIG. 1 shows growth inhibition of *Bacillus subtilis* var. locuses B1 and B2 by sophorolipids.

The subject invention provides environmentally-friendly compositions and methods to reduce and/or eliminate hydrogen sulfide ($H_2S$) and other sulfur-containing compounds in oil and natural gas while simultaneously enhancing oil recovery. In one embodiment, this is achieved by the efficient control of sulfate reducing bacteria (SRB). The compositions and methods can also be used for reducing the "sourness" of crude oil and gas.

The present invention further provides compositions and methods for reducing and/or eliminating microbial induced corrosion ("MIC").

The methods and compositions can be used in the oil and gas industry, agriculture, environmental cleanup, and other industries where biofilm and other microbial growth causes complications such as, for example, production of toxic byproducts such as $H_2S$ and mercaptans, corrosion of equipment, and reduction in quality of manufactured products.

In certain embodiments, the subject invention provides materials and methods for improving the quality of oil and/or gas while enhancing oil recovery, by treating drilling sites with compositions comprising microorganisms and/or their by-products.

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In preferred embodiments, the microbes are present, with substrate in which they were grown, in the microbe-based composition. The cells may be present at, for example, a concentration of $1 \times 10^4$, $1 \times 10^5$, $1 \times 10^6$, $1 \times 10^7$, $1 \times 10^8$, $1 \times 10^9$, $1 \times 10^{10,}$ or $1 \times 10^{11}$ or more propagules per milliliter of the composition. As used herein, a propagule is any portion of a microorganism from which a new and/or mature organism can develop, including but not limited to, cells, spores, conidia, mycelia, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, "harvested" in the context of fermentation of microorganisms refers to removing some or all of the microbe-based composition from a growth vessel.

In some embodiments, the microbes used according to the subject invention are "surfactant over-producing." For example, the strain may produce at least 0.1-10 g/L, e.g., 0.5-1 g/L surfactant. For example, the bacteria may produce at least 10%, 25%, 50%, 100%, 2-fold, 5-fold, 7.5 fold, 10-fold, 12-fold, 15-fold or more surfactant compared to other oil-recovery microbial strains. Specifically, *Bacillus subtilis* ATCC 39307 is used herein as a reference strain.

As used herein, "applying" a composition or product refers to contacting it with a target or site such that the composition or product can have an effect on that target or site. The effect can be due to, for example, microbial growth and/or the action of a biosurfactant or other growth by-product. For example, the microbe-based compositions or products can be injected into oil wells and/or the piping, pumps, tanks, etc. associated with oil wells.

As used herein, "surfactant" refers to a compound that lowers the surface tension (or interfacial tension) between two liquids or between a liquid and a solid. Surfactants act as detergents, wetting agents, emulsifiers, foaming agents, and/or dispersants. A surfactant produced by microorganisms is referred to as a "biosurfactant."

As used herein, a "mercaptan" is another term for a thiol. Mercaptans are organosulfur compounds that contain a carbon-bonded sulfhydryl group. Their chemical structure is similar to alcohols, but comprises a sulfur atom in place of the oxygen atom. Some mercaptans, particularly pure forms, present strong unpleasant odors, resembling garlic or rotten eggs. Others are responsible for the aromas of roasted coffee or grapefruit. Humans are highly sensitive to mercaptans, even at very low levels. Any reference to H2S within the subject application shall include mercaptans and other sulfur-containing compounds.

As used herein, a "biofilm" is a complex aggregate of microorganisms, such as bacteria, wherein the cells adhere to each other on a surface. The cells in biofilms are physiologically distinct from planktonic cells of the same organism, which are single cells that can float or swim in liquid medium.

As used herein, "oil and natural gas production" refers to any and all operations involved in the extraction of crude oil and/or natural gas from the earth, processing, and through its eventual purchase and use by consumers. Oil and natural gas production can include, but is not limited to, drilling, pumping, recovering, fracking, water-flooding, transmission, processing, refining, transportation, and storage of oil and/or gas.

A "metabolite" refers to any substance produced by metabolism or a substance necessary for taking part in a particular metabolic process. A metabolite can be an organic compound that is a starting material (e.g., glucose), an intermediate (e.g., acetyl-CoA), or an end product (e.g., n-butanol) of metabolism. Examples of metabolites can include, but are not limited to, enzymes, toxins, acids, solvents, alcohols, proteins, carbohydrates, vitamins, minerals, microelements, amino acids, polymers, and surfactants.

An "oil and natural gas production environment" refers to any environment, equipment, structure, or surface, whether naturally-occurring or man-made, wherein one or more aspects of oil and natural gas production and processing occur, including but not limited to, oil and gas-containing formations, drilling rigs, petroleum refineries, wellbores, oil well rods, flow lines, separators, pumps, pipes, tubing, casing, valves, fittings, gathering systems, and storage tanks.

As used herein, the term "control" used in reference to the activity produced by biosurfactants or biosurfactant-producing microorganisms extends to the act of killing, disabling, immobilizing, or reducing population numbers of an organism, or otherwise rendering the organism substantially incapable of causing harm. With regard to a biofilm, control can further refer to disrupting the formation of biofilms, and/or dismantling an existing biofilm.

As used herein, the term "biocorrosive bacteria" or "biocorrosive microorganism" means, any taxonomic grouping of bacteria (or microorganism) known to contribute to microbial induced corrosion ("MIC") of metallic and/or non-metallic materials. Non-limiting examples include chemoautotrophs, sulfate-reducing bacteria, iron oxidizing bacteria, sulfur oxidizing bacteria, nitrate reducing bacteria, methanogens, and acid producing bacteria. These bacteria are capable of reducing metal directly, producing metabolic products that are corrosive (e.g., hydrogen sulfide gas), and/or leading to the formation of biofilms that can alter the local environment to promote corrosion.

As used herein, the phrase "improving the quality" in reference to the quality of oil and/or gas can include reducing the conversion of sweet oil and gas to sour oil and gas, increasing the conversion of sour oil and gas to sweet oil and gas, preserving the sweetness of oil and gas, reducing the concentration of sulfur-containing compounds such as hydrogen sulfide and mercaptans in the oil and/or gas (either within the well or outside of the well, e.g., in a storage tank), and inhibiting growth of SRB and other biocorrosive bacteria in the oil and gas.

Compositions for Reducing Hydrogen Sulfide and Mercaptans

The subject invention provides advantageous uses for microbes, as well as the by-products of their growth, such as biosurfactants. In certain embodiments, the subject invention provides microbe-based products, as well as their uses in improved oil production. In specific embodiments, the methods and compositions described herein utilize microorganisms and/or their growth byproducts to improve the quality of oil and gas, improve the integrity of equipment used for producing oil and gas, and enhance the recovery of oil and gas from a formation.

In preferred embodiments of the subject invention, a first and a second composition are provided for reducing $H_2S$ and mercaptans, and controlling biocorrosive bacteria present in oil and natural gas production environments. Due to reduced concentrations of $H_2S$, the compositions can further prevent, reduce and/or eliminate the corrosion and deterioration of equipment and structures in, and on, which biocorrosive bacteria grow, particularly those that are made of metal. In a specific embodiment, the compositions can be used to reduce MIC and deterioration of equipment and structures used for oil and natural gas production.

In preferred embodiments, the first composition comprises an antimicrobial biosurfactant blend, a chelating agent, and one or more $H_2S$ scavengers.

In some embodiments, the antimicrobial biosurfactant blend comprises one or more biosurfactants. Preferably, the one or more biosurfactants comprise at least one glycolipid and at least one lipopeptide. Advantageously, the biosurfactants can be used at relatively low concentrations to inhibit the growth of bacteria, including Gram-negative and Gram-positive bacteria.

Biosurfactants are a structurally diverse group of surface-active substances produced by microorganisms. All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and change the properties of bacterial cell surfaces.

Biosurfactants accumulate at interfaces, thus reducing interfacial tension and leading to the formation of aggregated micellular structures in solution. The ability of biosurfactants to form pores and destabilize biological membranes permits their use as antibacterial, antifungal, and hemolytic agents. Combined with the characteristics of low toxicity and biodegradability, biosurfactants are advantageous for use in the oil and gas industry as effective inhibitors of SRB growth and a resulting reduction of hydrogen sulfide production.

Biosurfactants include low molecular weight glycolipids, lipopeptides, flavolipids, phospholipids, and high molecular weight polymers such as lipoproteins, lipopolysaccharide-protein complexes, and polysaccharide-protein-fatty acid complexes. The hydrocarbon chain of a fatty acid acts as the common lipophilic moiety of a biosurfactant molecule, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

Microbial biosurfactants are produced by a variety of microorganisms, such as bacteria, fungi, and yeasts. Exemplary biosurfactant-producing microorganisms include *Pseudomonas* spp. (*P. aeruginosa, P. putida, P. florescens, P. fragi, P. syringae*); *Pseudozyma* spp. (*P. aphidis*); *Flavobacterium* spp.; *Pichia* spp. (*P. anomala, P. lynferdii, P. guilliermondii, P. sydowiorum*), *Bacillus* spp. (*B. subtilis, B. amyloliquefaciens, B. pumillus, B. cereus, B. licheniformis*); *Wickerhamomyces* spp. (*W. anomalus*); *Starmerella* spp. (*S. bombicola*); *Candida* spp. (*C. albicans, C. rugosa, C. tropicalis, C. lipolytica, C. torulopsis*); *Rhodococcus* spp.; *Arthrobacter* spp.; *Campylobacter* spp.; *Cornybacterium* spp., and many others. The biosurfactants may be obtained by fermentation processes known in the art.

In some embodiments, the biosurfactants used in the antimicrobial blend include glycolipids such as rhamnolipids (RLP), sophorolipids (SLP), trehalose lipids or mannosylerythrithol lipids (MEL).

In certain embodiments, the one or more biosurfactants can include one or more glycolipids such as, for example, sophorolipids, rhamnolipids, or a combination thereof.

In some embodiments, the antimicrobial biosurfactant blend further comprises a lipopeptide biosurfactant, for example, surfactin or lichenysin. Various *Bacillus* bacteria are capable of producing lipopeptides, such as *B. subtilis, B. licheniformis*, and *B. amyloliquefaciens*, among others.

Surfactin in particular is one of a series of lipopeptide biosurfactants referred to as porens. It has antimicrobial, antiviral, antifungal properties, and in particular its antibacterial effects on both Gram-positive and Gram-negative bacteria. Thus, the use of surfactin broadens the spectrum of antimicrobial activity to include Gram-negative bacteria. Surfactin can be obtained from known fermentation processes in the art.

In some embodiments, the biosurfactants of the first composition are in a purified form. In other embodiments the biosurfactants are produced in situ by microorganisms present at the site of application.

The biosurfactants can be used to inhibit the growth of bacteria at relatively low concentrations. In preferred embodiments, the total biosurfactant concentration used in the subject composition is from 1,000 ppm to 3,000 ppm or more. In a specific embodiment, the biosurfactant concentration is about 2,500 ppm.

The blend of biosurfactants used in the subject invention can be formulated using any number of combinations and proportions. In certain embodiments, the biosurfactant blend comprises SLP, RLP and surfactin. In one embodiment, the biosurfactant blend comprises SLP in a proportion of 30% to 90% of the blend. In one embodiment, the biosurfactant blend comprises RLP in a proportion of 10% to 60% of the blend. In one embodiment, the biosurfactant blend comprises surfactin in a proportion of 2% to 40% of the blend. In one embodiment, the biosurfactant blend comprises SLP, RLP and surfactin at a ratio of 60/30/10%. In another embodiment, the biosurfactant blend comprises SLP, RLP and surfactin at a ratio of 40/40/20%. In preferred embodiments, the biosurfactant blend comprises SLP, RLP and surfactin at a ratio of 15:1:1.

In some embodiments, the composition further comprises a chelator or chelating agent. As used herein, "chelator" or "chelating agent" means an active agent capable of removing a metal ion from a system by forming a complex so that the metal ion cannot readily participate in or catalyze oxygen radical formation.

Examples of chelating agents suitable for the present invention include, but are not limited to, dimercaptosuccinic acid (DMSA), 2,3-dimercaptopropanesulfonic acid (DMPS), alpha lipoic acid (ALA), thiamine tetrahydrofurfuryl disulfide (TTFD), penicillamine, ethylenediaminetetraacetic acid (EDTA), and citric acid.

Advantageously, the chelating agent enhances the efficacy of the antimicrobial biosurfactant blend by modifying the cell walls of, for example, Gram-negative bacteria, to be more susceptible to surfactant treatment. Consequently, the ability to permeate Gram-negative bacteria broadens the spectrum of antimicrobial capabilities for the subject invention.

The chelating agent can be added to the composition in amounts up to about 5 g/L or more. In specific embodiments, the chelating agent is EDTA at a concentration of about 4 g/L to about 5 g/L.

In some embodiments, the composition further comprises one or more $H_2S$ scavengers. As used herein, "hydrogen sulfide scavenger" refers to any chemical that can react with one or more sulfur-containing species, including mercaptans, and can convert it to a more inert form. Effective scavenging is based on attaining an irreversible and complete chemical reaction between the scavenger and one or more sulfur-containing species.

The one or more $H_2S$ scavengers utilized in the subject composition can be, for example, nitrate or nitrite solutions. In certain embodiments, the $H_2S$ scavengers are selected from glyoxal and nitrate or nitrite salts, including but not limited to, sodium nitrate, sodium nitrite, ammonium nitrate, ammonium nitrite, potassium nitrate, and potassium nitrite. In specific embodiments, the $H_2S$ scavenger is 5 g/L potassium nitrate and/or 5 g/L sodium nitrate and/or 5 g/L glyoxal.

In one embodiment, the potency of the first composition's antimicrobial effects can be further enhanced by the addition of one or more natural biological substances with known antimicrobial properties, including antimicrobial properties against Gram-negative microorganisms.

In one embodiment, the natural biological substance can comprise nisin, an antimicrobial polypeptide obtained by cultivation of *Lactococcus lactis*. Total concentration of nisin included in the first composition can be at least 200 ppm, 250 ppm, 300 ppm, or greater.

In one embodiment, the natural biological substance is citronella (lemongrass extract). Citronella is an inexpensive, plant-derived substance that can be used for suppressing both Gram-negative and Gram-positive bacteria, as well as some fungi and yeasts. Total concentration of citronella included in the first composition can be about 30 ppm to about 100 ppm, preferably about 50 ppm.

In one embodiment, the first composition can comprise any number of the above described biosurfactants, chelators, natural antimicrobial substances, and hydrogen sulfide scavengers, in any combination, such that the broadest possible spectrum of biocorrosive bacteria can be controlled and the greatest amount of hydrogen sulfide and mercaptans can be reduced.

In one embodiment a second composition is provided, comprising a microorganism capable of outcompeting residual SRB for common carbon and energy sources, for example, a nitrogen-reducing bacteria, thereby suppressing the regrowth of the SRB; and, optionally, nutrient sources for ensuring effective growth of microorganism in anaerobic conditions.

In one embodiment, the microorganism used in the second composition comprises a strain of *Bacillus* capable of producing lipopeptide biosurfactants, for example, *B. subtilis*, *B. licheniformis*, *B. firmus*, *B. laterosporus*, *B. megaterium*, and/or *B. amyloliquefaciens*. Preferably, the *Bacillus* strain is selected from *Bacillus subtilis* var. locuses strains B1 and/or B2, which are effective producers of surfactin.

In one embodiment, B1 and/or B2 serve as nitrate-reducing bacteria ("NRB"). In preferred embodiments, the initial stable growing concentration of B1 and/or B2 within the second composition is between $10^5$ to $10^7$ CFU/ml. Even more preferably, the initial stable growing concentration of B1 and/or B2 is at least $10^6$ CFU/ml of the second composition.

In some embodiments, the *Bacillus* strains used according to the subject invention are capable of thriving under low oxygen and/or high salt conditions. Thus, in some embodiments, the *Bacillus* strain is grown under anaerobic conditions.

Use of other *Bacillus* species, such as *B. licheniformis*, which produces lichenysin, and *B. amyloliquefaciens*, which produces cyclic lipopeptides and fengycin, is also envisioned with the subject invention.

In one embodiment, the second composition further comprises nutrient sources, including but not limited to, nitrites, nitrates, phosphorus, magnesium, protein sources and/or carbon.

In one embodiment, the nutrient sources are added to the second composition as follows: about 1.0 to about 10 g/L of $NH_4NH_3$; at least 0.5 g/L of $KNO_3$, at least 0.2 g/L of $Mg(NO_3)_2$, and about 2.0 to about 6.0 g/L of a carbohydrate, such as molasses or glucose, and 0.1-0.5 g/L of yeast extract.

In one embodiment, the second composition further comprises one or more substances for enhancing germination of the microorganism. That is, activation and/or sporulation of the microbes can be enhanced by adding micromolar amounts of L-alanine, manganese, L-valine, and L-asparagine or any other known germination enhancer to the second composition.

Other microbial strains including, for example, other bacterial strains capable of accumulating significant amounts of, for example, glycolipid and/or lipopeptide-biosurfactants can be used in accordance with the subject invention. For example, the *Bacillus* strains may be used alone, or in combination with another microorganism, such as a *Pseudomonas* clade bacterium. *Pseudomonas aeruginosa*, for example, is an effective producer of rhamnolipids.

Other biosurfactants useful according to the present invention include mannoprotein, beta-glucan and other metabolites that have bio-emulsifying and surface/interfacial tension-reducing properties.

Advantageously, in one embodiment, the subject compositions and methods can be used to prevent SRB species in oil and gas production environments and oil and gas formations from developing resistance to antibacterial treatments.

Advantageously, the present compositions can be used without releasing large quantities of inorganic compounds into the environment. Additionally, the compositions utilize components that are biodegradable and toxicologically safe.

Thus, the present invention can be used in all operations of oil and gas production as a "green" treatment.

Sulfur Reducing Bacteria and MIC

In one embodiment, the composition can be used to control SRB and other biocorrosive bacteria. In one embodiment, the biocorrosive bacteria are in the form of a biofilm.

Many SRB belong to the phylum Proteobacteria. Of those, one group of obligate anaerobes fall within the class Deltaproteobacteria. This group includes Desulfuromonas, Desulfurella, Geobacter, and Pelobacter. Other Proteobacteria classes comprise microaerophiles, which include Wolinella, Campylobacter, Shewanella, Sulfurospirillum, and Geospirillum bamesi.

Many other SRB belong to archaea from a phylogenetically diverse class and belong (but are not limited to) the following orders: Thermococcales, Thermoproteales, Pyrodictales, and Sulfolobales. Moreover, SRB are found in several other phylogenetic lines. Currently, 60 genera containing more than 220 species of SRB are known.

In certain embodiments, the compositions of the subject invention can have broad-spectrum antimicrobial properties, meaning they can be used to control both Gram-positive and Gram-negative bacteria, as well as other biocorrosive microorganisms. Further examples of microorganisms that can be controlled by the present composition, which are responsible for deterioration processes in natural gas and oil and which have been isolated from oil, brine water, petroleum and gas equipment include, but are not limited to, the following: *Methanobacterium curvum, Methanocalculus halotolerans, Methanoculleus* spp., *Methanofollis* spp. (e.g., *M. liminatans*), *Methanosarcina* spp. (e.g., *M. barkeri, M. siciliae*), *Methanospirillum hungatei, Anaerobaculum mobile, Thermodesulfovibrio yellowstonii, Desulfovibrio* spp. (e.g., *D. vulgaris*), *Thermotoga* spp. (e.g., *T. hypogea, T. neapaitan*), *Clostridium* spp. (e.g., *C. sporogenes, C. bifermentas, C. celerecrescens*), *Desulfotomaculum* spp. (e.g., *D. kuznetsorii*), *Desulfovibrio desulfuricans, Citrobacter freundii, Cetobacterium somerae, Klebsiella pneumonia, Acinetobacter* spp. (e.g., *A. junii*), *E. coli*, and *Staphylococcus auriculari*.

In one embodiment, the composition can inhibit $H_2S$ production by SRB and other biocorrosive bacteria by controlling the biocorrosive bacteria. In another embodiment, the composition can reduce the concentration of hydrogen sulfide present in an oil containing formation or in oil production equipment.

Cultivation of Microorganisms

In some embodiments, methods are provided for cultivating microorganisms and/or producing their growth by-products, for example, biosurfactants, for use in the subject compositions and methods. The microorganisms grown according to the subject invention can be spore-forming bacteria. These microorganisms may be natural, or genetically modified microorganisms. For example, the microorganisms may be transformed with specific genes to exhibit specific characteristics. The microorganisms may also be mutants of a desired strain. Procedures for making mutants are well known in the microbiological art. For example, ultraviolet light and nitrosoguanidine are used extensively toward this end.

In preferred embodiments, the microorganisms are bacteria, including Gram-positive and Gram-negative bacteria. The bacteria may be, for example *Bacillus* (e.g., *B. subtilis, B. licheniformis, B. firmus, B. laterosporus, B. megaterium, B. amyloliquifaciens*), *Clostridium* (e.g., *C. butyricum, C. tyrobutyricum, C. acetobutyricum, Clostridium* NIPER 7, and *C. beijerinckii*), *Azobacter* (e.g., *A. vinelandii, A. chroococcum*), *Pseudomonas* (e.g., *P. chlororaphis* subsp. *aureofaciens* (Kluyver), *P. aeruginosa*), *Agrobacterium radiobacter, Azospirillumbrasiliensis, Rhizobium, Sphingomonas paucimobilis, Ralslonia eulropha*, and/or *Rhodospirillum rubrum*.

In specific embodiments, the microbe is a strain of *Bacillus* capable of producing lipopeptide biosurfactants, for example, *B. subtilis, B. licheniformis, B. firmus, B. laterosporus, B. megaterium*, and/or *B. amyloliquefaciens*. Preferably, the *Bacillus* strain is selected from *Bacillus subtilis* var. locuses strains B1 and/or B2, which are effective producers of surfactin.

Use of other *Bacillus* species, such as *B. licheniformis*, which produces lichenysin, and *B. amyloliquefaciens*, which produces cyclic lipopeptides and fengycin, is also envisioned with the subject invention.

In one embodiment, the microbe is a non-pathogenic strain of *Pseudomonas*, such as, e.g., *P. aeruginosa*. Preferably, the *Pseudomonas* strain is a producer of rhamnolipid (RLP) bio surfactants.

The subject invention utilizes methods for cultivation of microorganisms and production of microbial metabolites and/or other by-products of microbial growth. The subject invention further utilizes cultivation processes that are suitable for cultivation of microorganisms and production of microbial metabolites on a desired scale. The microbial cultivation systems would typically use submerged culture fermentation; however, surface culture and hybrid systems can also be used. As used herein "fermentation" refers to growth of cells under controlled conditions. The growth could be aerobic or anaerobic.

In one embodiment, the compositions according to the subject invention are obtained through cultivation processes ranging from small to large scales. These cultivation processes include, but are not limited to, submerged cultivation, surface cultivation, solid state fermentation (SSF), and combinations thereof.

In one embodiment, the subject invention provides materials and methods of producing a biosurfactant by cultivating a microbe strain of the subject invention under conditions appropriate for growth and biosurfactant production; and purifying the biosurfactant. The subject invention also provides methods of producing enzymes or other metabolites by cultivating a microbe strain of the subject invention under conditions appropriate for growth and metabolite expression; and purifying the enzyme or other metabolite.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g. measurement of cell number and growth phases). Alternatively, a daily sample may be taken from the vessel and subjected to enumeration by techniques known in the art, such as dilution plating technique. Dilution plating is a simple technique used to estimate the number of bacteria in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method of cultivation can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, and/or linseed oil. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included, e.g., L-Alanine.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before, and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

The biomass content of the fermentation broth may be, for example from 5 g/l to 180 g/l or more. In one embodiment, the solids content of the broth is from 10 g/l to 150 g/l.

In one embodiment, the subject invention further provides a method for producing microbial metabolites such as ethanol, lactic acid, beta-glucan, proteins, peptides, metabolic intermediates, polyunsaturated fatty acid, and lipids. The metabolite content produced by the method can be, for example, at least 20%, 30%, 40%, 50%, 60%, 70%, 80%, or 90%.

The microbial growth by-product produced by microorganisms of interest may be retained in the microorganisms or secreted into the liquid medium. In another embodiment, the method for producing microbial growth by-product, such as biosurfactants, may further comprise steps of concentrating and purifying the microbial growth by-product of interest. In a further embodiment, the liquid medium may contain compounds that stabilize the activity of microbial growth by-product.

In one embodiment, all of the microbial cultivation composition is removed upon the completion of the cultivation (e.g., upon, for example, achieving a desired spore density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells. In this manner, a quasi-continuous system is created.

Advantageously, the method does not require complicated equipment or high energy consumption. The microorganisms of interest can be cultivated at small or large scale on site. Similarly, the microbial metabolites or other by-products can also be produced at large quantities at the site of need.

Advantageously, the microbe-based products can be produced in remote locations. The microbe growth facilities may operate off the grid by utilizing, for example, solar, wind and/or hydroelectric power.

Preparation of Microbe-Based Products

One microbe-based product of the subject invention is simply the fermentation broth containing the microorganism and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

The microorganisms in the microbe-based product may be in an active or inactive form. Preferably, the microorganisms are in the spore form.

The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes and/or broth resulting from the microbial growth can be removed from the growth vessel and transferred via, for example, piping for immediate use.

In other embodiments, the microbes and/or broth can be placed in containers of appropriate size, taking into consideration, for example, the intended use, the contemplated method of application, the size of the fermentation tank, and any mode of transportation from microbe growth facility to the location of use. Thus, the containers into which the microbe-based product is placed may be, for example, from 1 gallon to 1,000 gallons or more. In other embodiments the containers are 2 gallons, 5 gallons, 25 gallons, or larger.

Upon harvesting the microbes and/or broth from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

Other suitable additives, which may be contained in the formulations according to the invention, include substances that are customarily used for such preparations. Example of such additives include surfactants, emulsifying agents, lubricants, buffering agents, solubility controlling agents, pH adjusting agents, preservatives, stabilizers and ultra-violet light resistant agents.

In one embodiment, the product may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid and mixtures thereof.

The pH of the microbe-based product should be suitable for the microorganism of interest. In a preferred embodiment, the pH of the microbe-based composition ranges from 7.0-7.5.

In one embodiment, additional components such as an aqueous preparation of a salt, e.g., sodium bicarbonate or carbonate, sodium sulfate, sodium phosphate, or sodium biphosphate, can be included in the formulation.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

Local Production of Microbe-Based Products

In preferred embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The distributed microbe growth facilities of the subject invention can be located at the location where the microbe-based product will be used. For example, the microbe growth facility may be less than 300, 250, 200, 150, 100, 75, 50, 25, 15, 10, 5, 3, or 1 mile from the location of use.

Because the microbe-based product is generated locally, without resort to the microorganism stabilization, preservation, storage and transportation processes of conventional microbial production, a much higher density of vegetative cells, reproductive spores, mycelia, conidia, and/or other microbial propagules can be generated, thereby requiring a smaller volume of the microbe-based product for use in the on-site application or which allows much higher density microbial applications where necessary to achieve the desired efficacy. This allows for a scaled-down bioreactor (e.g., smaller fermentation tank, and smaller supplies of starter material, nutrients, pH control agents, and defoaming agents) that makes the system efficient. Local generation of the microbe-based product also facilitates the inclusion of the growth broth in the product. The broth can contain agents produced during the fermentation that are particularly well-suited for local use.

Locally-produced high density, robust cultures of microbes are more effective in the field than those that have undergone vegetative cell stabilization or have sat in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the broth in which the microbes are grown. If desired, the compositions can have a high density of vegetative cells, reproductive cells, spores, mycelia, conidia, or a mixture thereof.

Advantageously, the compositions can be tailored for use at a specified location. In one embodiment, the microbe growth facility is located on, or near, a site where the microbe-based products will be used.

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated broth and metabolites in which the cells are originally grown.

Advantageously, in preferred embodiments, the systems of the subject invention harness the power of naturally-occurring local microorganisms and their metabolic by-products to improve oil production.

The cultivation time for the individual vessels may be, for example, from 1 to 7 to 14 days or longer. The cultivation product can be harvested in any of a number of different ways.

Because the microbe-based product is generated on-site or near the site of application, without the requirement of stabilization, preservation, prolonged storage and extensive transportation processes of conventional production, a much higher density of live microorganisms can be generated, thereby requiring a much smaller volume of the microbe-based product for use in an on-site application. This allows for a scaled-down bioreactor (e.g. smaller fermentation tank, smaller supplies of starter material, nutrients, pH control agents, and de-foaming agent, etc.), no reason to stabilize the cells or separate them from their culture broth and can facilitate the portability of the product, if desired.

The microbe growth facilities provide manufacturing versatility by the ability to tailor the microbe-based products to improve synergies with destination geographies.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

Local microbes can be identified based on, for example, salt tolerance, ability to grow at high temperatures.

In one embodiment, the composition according to the subject invention is obtained through cultivation processes ranging from small (e.g., lab setting) to large (e.g., industrial setting) scales. These cultivation processes include, but are not limited to, submerged cultivation/fermentation, surface cultivation, solid state fermentation (SSF), and combinations thereof.

Methods for Reducing Sulfur-Containing Compounds, Inhibiting MIC and Enhancing Oil and Gas Recovery In one embodiment, a two-phase method is provided for improving oil and natural gas production. Specifically, the methods can be used to inhibit $H_2S$ production by SRB and other biocorrosive bacteria, as well as reduce the "sourness" of crude oil and gas, while simultaneously enhancing oil and gas recovery. The methods can further be used to reduce the conversion of sweet oil to sour oil and gas, increase the conversion of sour oil and gas to sweet oil and gas, and/or preserve the sweetness of oil and gas. The methods can further be used to reduce the content of $H_2S$ and mercaptans in oil within or outside of a well.

In certain embodiments, the two-phase method can further be used for reducing and/or eliminating microbial induced corrosion ("MIC") of equipment and structures used for crude oil and natural gas production.

In one embodiment, phase one of the method comprises applying the first composition of the subject invention to an oil and gas containing formation, for example, by injecting the first composition as deeply as possible into a wellbore; shutting in the formation; pumping out the composition; and opening the formation to resume oil and/or gas recovery.

In preferred embodiments, the composition utilized in phase one (i.e., the first composition of the subject invention) comprises an antimicrobial biosurfactant blend, a chelating agent, and one or more $H_2S$ scavengers.

In one embodiment, the antimicrobial biosurfactant blend comprises one or more biosurfactants selected from glycolipids, e.g., sophorolipids, rhamnolipids, and/or a combination thereof, and lipopeptides, e.g., surfactin, lichenysin, fengycin and/or a combination thereof.

In one embodiment, the chelating agent is EDTA.

In one embodiment, the one or more $H_2S$ scavengers are selected from glyoxal and nitrate or nitrite salts, including but not limited to, sodium nitrate, sodium nitrite, ammonium nitrate, ammonium nitrite, potassium nitrate, and potassium nitrite.

In one embodiment, the first composition further comprises one or more natural biological substances with known antimicrobial properties, such as, for example, nisin and/or citronella (lemongrass extract).

Preferably, phase one is carried out while continuously monitoring hydrogen sulfide levels within the formation.

In one embodiment of phase one, the step of shutting in the formation is carried out until the level of hydrogen sulfide reduces to a desired concentration. For example, the shut in period can endure for about 3 to about 60 days, or until the hydrogen sulfide levels reduce to a concentration of about 0 ppm to about 50 ppm, preferably from about 0 ppm to about 25 ppm.

Phase one of the method is designed as initial treatment to (a) control biocorrosive bacteria, such as SRB, (b) reduce $H_2S$ concentration in the formation, and (c) enhance oil and gas recovery from the formation.

In one embodiment, phase two of the method comprises recovering oil and/or gas from the formation until an increase of hydrogen sulfide concentration is observed; applying the second composition of the subject invention to the formation, for example, by injecting it as deeply as possible into the wellbore; shutting in the formation; and opening the formation to resume oil and/or gas recovery.

Preferably, phase two is carried out while continuously monitoring hydrogen sulfide levels within the formation.

In one embodiment, the composition utilized in phase two (i.e., the second composition of the subject invention) comprises a microorganism capable of outcompeting residual SRB for common carbon and energy sources, thereby suppressing the regrowth of SRB; and, optionally, nutrient sources for ensuring effective growth of the microbial culture in anaerobic conditions, including but not limited to, nitrites, nitrates, phosphorus, magnesium, protein sources and/or carbon.

In one embodiment, the nutrient sources are included in the second composition as follows: about 1.0 to about 10 g/L of $NH_4NO_3$; at least 0.5 g/L of $KNO_3$; at least 0.2 g/L of $Mg(NO_3)_2$; and about 2.0 to about 6.0 g/L of a carbohydrate, such as molasses or glucose, and 0.1-0.5 g/L of yeast extract.

Preferably, the microorganism of the second composition is in spore form. Accordingly, in one embodiment, the second composition can comprise substances for enhancing germination of spores, such as, for example, L-alanine and/or manganese.

In one embodiment, the microorganism of the second composition is a spore-forming, biosurfactant-producing strain of bacteria. In preferred embodiments, the bacteria can be introduced as nitrate-reducing bacteria ("NRB").

In one embodiment, the bacteria is a species of the *Bacillus* clade. In preferred embodiments, the bacteria of the second composition is a strain of *Bacillus subtilis*. Even more specifically, the *Bacillus subtilis* can be *B. subtilis* var. locuses strains B1 and/or B2, which are effective producers of the lipopeptide surfactin.

In one embodiment, the bacteria is a strain of *Pseudomonas,* such as, for example, *P. aeruginosa. P. aeruginosa* is an effective producer of rhamnolipid biosurfactants.

In one embodiment, the second composition comprises a combination of a *Bacillus* clade bacteria and a *Pseudomonas* clade bacteria.

In one embodiment, the bacterial spores germinate and multiply while producing biosurfactants, such as surfactin and/or rhamnolipid, in situ. Thus, phase two enhances the methods by broadening the spectrum of antimicrobial capabilities to both Gram-positive and Gram-negative bacteria. As a result, the recovery of crude oil and natural gas from oil and gas containing formations is also enhanced.

In one embodiment, the increase of hydrogen sulfide concentration that is observed prior to application of the second composition in phase two is an increase of from about 1 ppm to about 50 ppm to about 100 ppm, or higher, above the lowest observed concentration. In one embodiment, the increase of hydrogen sulfide concentration that is observed prior to application of the second composition is any increase that brings the concentration of hydrogen sulfide to a level of about 50 to about 100 ppm, or higher.

In one embodiment of phase two, the step of shutting in the formation is carried out until the level of hydrogen sulfide reduces to a desired concentration. For example, the shut in period can endure for about 3 to about 60 days, or until the hydrogen sulfide levels reduce to a concentration of about 0 ppm to about 50 ppm, preferably from about 0 ppm to about 25 ppm.

Phase two of the method is designed to repopulate the wellbore and/or reservoir with beneficial bacterial that can outcompete and overgrow any remaining SRB. Phase two can also serve to stabilize and prolong the antimicrobial and hydrogen sulfide-reducing effects of phase one, for example, by preventing any remaining SRB from multiplying. Thus, phase two further enhances control of biocorrosive bacteria, reduction in hydrogen sulfide concentration, and oil and gas recovery.

In one embodiment of the subject method, only phase one is employed without phase two. In one embodiment, phase two is employed without phase one beforehand. In other words, if it is determined that sufficient hydrogen sulfide reduction has occurred with use of phase one alone, phase two may optionally be omitted, or delayed, until it is determined that hydrogen sulfide levels are increasing and/or a decline in oil recovery is occurring.

In certain embodiments, the first and/or second compositions can be applied in an amount ranging from 50 BBL to 1,000 BBL to 10,000 BBL, depending on the amount of hydrogen sulfide present. In preferred embodiments, the first and/or second compositions are applied in a range between 50 to 1,000 BBL.

In one embodiment, a step of determining the amount of hydrogen sulfide (e.g., in ppm) present in the formation is performed prior to phase one and/or phase two of the subject method, followed by a step of determining the volume of treatment composition needed.

The application of the compositions of the subject invention can be performed during drilling operations (e.g., while drilling, while tripping-in or tripping-out of the hole, while circulating mud, while casing, while placing a production liner, and/or while cementing, etc.), and/or as a production treatment. Application can comprise pumping for as long as 1 hour, 5 hours, 10 hours or more, depending upon the amount of composition being applied.

Furthermore, application can be performed to any piece of oil and gas production equipment, for example, to a wellbore, casing, annulus, tubing, tank, flowline, and/or separator.

In preferred embodiments, the method further comprises, after completion of phase two, a step of continually monitoring H2S concentrations in the formation for any number of days or months after treatment to ensure hydrogen sulfide levels remain controlled. If hydrogen sulfide levels begin to increase again, the methods can be repeated as many times as necessary.

In one embodiment, the method can be utilized in non-well settings to control $H_2S$ and/or mercaptans present in oil and gas. By applying the first and second compositions to oil and/or gas outside of a well, for example, after extraction from a well or during storage, the microbes of the subject invention can sequester the $H_2S$ and/or mercaptans so that they precipitate out as salts.

In one embodiment the hydrogen sulfide content of natural gas, in particular, can be reduced using a biological scrubber and the compositions of the present invention. Biological scrubbers utilize microbial fixation to desulfurize natural gas. In certain scrubbers, the gas is streamed through a vessel containing media, such as a screen or a liquid matrix, on or in which microorganisms, such as those according to the present invention, are encouraged to grow. Air is then injected into the vessel and hydrogen sulfide in the gas is oxidized by chemical and biological reactions.

Further Definitions

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Growth Inhibition Effect of Biosurfactant to Gram-Positive Bacteria

A lawn of Gram-positive *Bacillus subtilis* B1 and B2 was plated. 20 μL of 2% sophorolipids were dropped at the center of the plate and incubated overnight at 40° C.

After the overnight cultivation, as shown in FIG. 1, a clear zone at the center of the lawn was present, indicating that sophorolipids can effectively inhibit the growth of or kill *B. subtilis*.

Example 2—Production of *Bacillus Subtilis*

Fermentation of *Bacillus subtilis* var. locuses can be performed in a 500 L reactor with 350 L of a nutrient medium containing (g/L):

| | |
|---|---|
| Glucose | 18 |
| Powder molasses | 2 |
| Sucrose | 1 |
| $KH_2PO_4$ | 0.5 |
| $Na_2HPO_4 \cdot 7H_2O$ | 2.1 |
| KCl | 0.1 |
| $MgSO_4$ | 0.5 |
| $CaCl_2$ | 0.05 |
| Urea | 2.5 |
| $NH_4Cl$ | 1.24 |
| Yeast extract | 2 |
| Corn peptone | 0.5 |
| TekNova trace element (mL) | 1 |

Temperature of cultivation is 40° C., pH stabilization is from 6.8-7.0, and DO stabilization is at 30% (concentration of oxygen in the air is taken as 100%). Duration of cultivation is 24-32 hours. The final concentration of bacterial culture is no less than $1 \times 10^9$ CFU/ml.

The amount of culture manufactured by a single fermentation cycle allows for the production of more than 2,000 barrels of final treatment formulation containing $10^6$ CFU of this strain of *Bacillus*.

Example 3—Complete Reduction of Hydrogen Sulfide in an Oil Field Using Phase One of the Two-Phase Method Prior to treatment, hydrogen sulfide level in a well measured 400 ppm. Eighty barrels of a treatment comprising 60% SLP, 30% RLP, and 10% surfactin were injected into the well over the course of approximately 5 hours. The well was then shut for 3 days. After resuming production of the well, hydrogen sulfide levels measured 0 ppm. This is phase one of the subject method.

The treatment can then be supplemented with phase two, wherein 1,000 barrels of *Bacillus subtilis*-based product (the second composition of the subject invention) is applied to the well over the course of approximately 8 hours. The nutrients can comprise, for example, 6 g glucose, 10 g/L ammonium nitrate, 0.1-0.5 g/L yeast extract, 0.5 g/L of $KNO_3$, and 0.2 g/L of $Mg(NO_3)_2$. The final concentration of biosurfactants in a wellbore can be approximately between 1,000-2,000 ppm and the final concentration of B1 can be, for example, $10^6$ cells/ml. The oil wells can then be shut down for 4-7 days, or as long as needed for the treatment to take effect.

Monitoring of wells can and should occur for any number of days or months after treatment to ensure hydrogen sulfide levels remain controlled.

Example 4—Well Stimulation and Hydrogen Sulfide Treatment in a Horizontal Well Using Two-Phase Method A horizontal well with hydrogen sulfide levels historically ranging from 200 to 400 ppm was treated with the subject two-phase methods. H2S levels were tested using a Draeger pump.

Phase One

Figure 2:
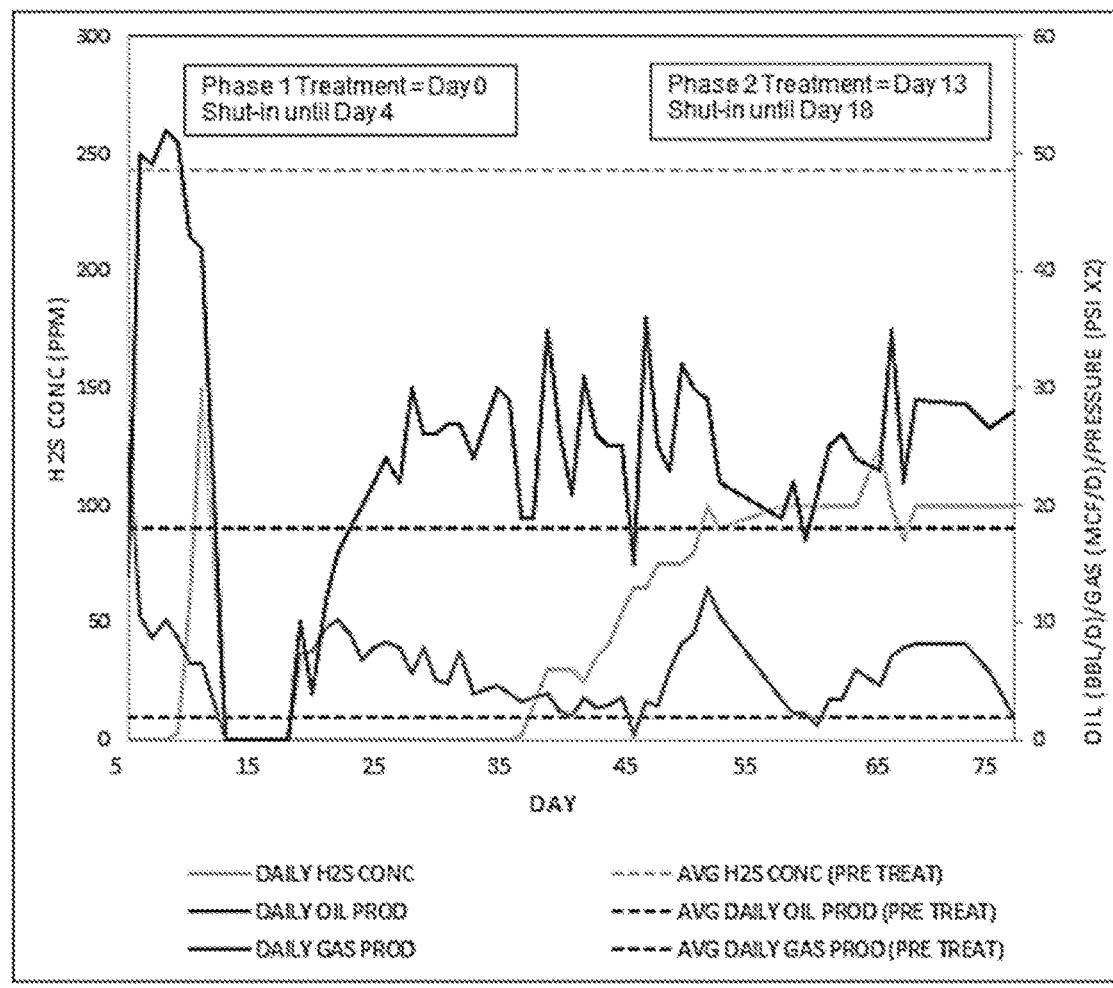
FIG. 2 shows daily oil production, gas production and H2S concentration before and after treatment with phase 1 and phase 2 of the subject methods in a horizontal well (Speechley Sand, Pa.).

On Day 0, H2S levels at the site were measured prior to treatment, as well as daily throughout treatment. A solvent truck was used to pump 70 BBL of the first composition of the subject invention into the casing of the wellbore. The biosurfactant blend of the first composition in this example comprise sophorolipid, rhamnolipid and surfactin at a ratio of 15:1:1. 10 BBL of the first composition was also pumped into the tank, flowline, and separator. The well was then shut in for 4 days. Pumping was then resumed until the treatment fluid was recovered. H2S and oil/gas production levels were measured daily (FIG. 2).

Phase Two

On Day 13, a 2,500 BBL certified clean frac tank was loaded with filtered brine. 60 BBL of nutrients was mixed with concentrated B1 using a pump truck. 863 BBL of the brine, nutrients and B1 composition was pumped down the casing at a rate of 3.4 to 4.0 BBL/min. The well was shut in for 5 days, after which normal pumping was resumed. H2S and oil and gas production levels were measured daily (FIG. 2).

Results

FIG. 2 shows measurements of H2S levels with daily oil and gas production. Since treatment with the subject methods, H2S rose slightly, but stayed relatively stable at 100 ppm.

We claim:

1. A method for reducing hydrogen sulfide and mercaptan concentration in an oil and/or natural gas production environment and also enhancing oil and/or gas recovery, wherein the method comprises:

applying a composition comprising an antimicrobial biosurfactant blend comprising sophorolipid, rhamnolipid and surfactin, EDTA as a chelating agent, and one or more hydrogen sulfide scavengers to an oil and/or gas containing formation; shutting in the formation; pumping out the composition; and opening the formation to resume oil and/or gas recovery.

2. The method of claim 1, wherein the hydrogen sulfide scavenger is glyoxal, potassium nitrate or sodium nitrate.

3. The method of claim 1, wherein the composition further comprises citronella and/or nisin.

4. The method of claim 1, which further comprises monitoring the level of hydrogen sulfide within the formation after applying the composition to the formation.

5. The method of claim 1, wherein the step of shutting in the formation is carried out for about 3 to about 60 days.

6. The method of claim 1, wherein the method reduces microbial induced corrosion (MIC).

7. The method of claim 1, used to control sulfate-reducing bacteria (SRB).

8. The method of claim 1, used to reduce corrosion in an oil field pipe line, tank, casing, tubing, rod, pump, and/or wellbore.

9. The method of claim 1, used to reduce the conversion of sweet oil to sour oil and/or increase the conversion of sour oil to sweet oil.

10. The method of claim 1, wherein prior to applying the composition to the formation, the method comprises the step of determining the amount of hydrogen sulfide within the formation.

\* \* \* \* \*